(12) United States Patent
Zhang

(10) Patent No.: US 10,954,282 B2
(45) Date of Patent: Mar. 23, 2021

(54) NBP158 AND USES THEREOF

(71) Applicant: Wentao Zhang, Walnut Creek, CA (US)

(72) Inventor: Wentao Zhang, Walnut Creek, CA (US)

( * ) Notice: Subject to any disclaimer, the term of this patent is extended or adjusted under 35 U.S.C. 154(b) by 663 days.

(21) Appl. No.: 15/527,643

(22) PCT Filed: Dec. 9, 2014

(86) PCT No.: PCT/CN2014/093344
§ 371 (c)(1),
(2) Date: May 17, 2017

(87) PCT Pub. No.: WO2016/090546
PCT Pub. Date: Jun. 16, 2016

(65) Prior Publication Data
US 2017/0327550 A1 Nov. 16, 2017

(51) Int. Cl.
| | | |
|---|---|---|
| C12N 15/00 | (2006.01) |
| C12N 15/09 | (2006.01) |
| C12N 5/00 | (2006.01) |
| C07K 14/00 | (2006.01) |
| C07K 14/50 | (2006.01) |
| C07K 14/47 | (2006.01) |
| A61K 38/18 | (2006.01) |
| C07K 14/475 | (2006.01) |
| A61K 38/00 | (2006.01) |

(52) U.S. Cl.
CPC ............. *C07K 14/50* (2013.01); *A61K 38/18* (2013.01); *C07K 14/47* (2013.01); *C07K 14/475* (2013.01); *C12N 15/09* (2013.01); *A61K 38/00* (2013.01)

(58) Field of Classification Search
None
See application file for complete search history.

(56) References Cited

U.S. PATENT DOCUMENTS

2009/0197256 A1    8/2009   Goppelt et al.
2013/0259923 A1*  10/2013   Bancel ................. A61K 48/005
                                          424/450

FOREIGN PATENT DOCUMENTS

| WO | 2014152089 A1 | 9/2014 |
| WO | 2014152090 A1 | 9/2014 |
| WO | 2014190147 A2 | 11/2014 |

OTHER PUBLICATIONS

The European Search Report dated Jun. 26, 2018.
Bin Xie et al: "Identification of the Fibroblast Growth Factor (FGF)-interacting Domain in a Secreted FGF-binding Jrotein by Phage Display", Journal of Biological Chemistry, vol. 281, No. 2, Oct. 27, 2005 (Oct. 27, 2005), pp. 1137-1144, XP055482044, IS ISSN: 0021-9258, DOI: 10.1074/jbc.M510754200.
Zhang Wentao, "Effect of FGF-binding protein 3 on vascular permeability", The Journal of Biological Chemistry, vol. vol.283, No. No. 42, Jul. 31, 2008, pp. 28329-28337.
Hanneken Anne, "Identification of soluble forms of the fibroblast growth factor receptor in blood", Proc.Natl.Acid.Sci.USA, vol. vol. 91, No. No. 19, Sep. 13, 1994, pp. 9170-9174.
Ohtsuki Kenzo, "Biochemical characterization of a N-terminal fragment (p5) cleaved from fibroblast growth factor-binding protein (FGF-BP) in bovine milk in vitro", Biochimica et Biophysica Acta, vol. vol. 1770, No. No. 8, May 22, 2007, pp. 1219-1229.
International Search Report for PCT/CN2014/093344, dated Aug. 28, 2015, ISA/CN.

* cited by examiner

*Primary Examiner* — Elizabeth C. Kemmerer
*Assistant Examiner* — Regina M DeBerry
(74) *Attorney, Agent, or Firm* — Yue (Robert) Xu; Apex Attorneys at Law, LLP

(57) ABSTRACT

This invention provides nucleic acid molecules encoding the N-terminal 158 amino acids of secreted human Fibroblast Growth Factor Binding Protein 3 (NBP158), pharmaceutical compositions comprising NBP158 polypeptide, and methods for treating metabolic disorders and conditions using such nucleic acids, polypeptides, or pharmaceutical compositions.

7 Claims, 7 Drawing Sheets

Specification includes a Sequence Listing.

(SEQ ID NO: 1)

| | | | | | | | | | | | | | | | | | | | |
|---|---|---|---|---|---|---|---|---|---|---|---|---|---|---|---|---|---|---|---|
| Met | Thr | Pro | Pro | Lys | Leu | Arg | Ala | Ser | Leu | Ser | Pro | Ser | Leu | Leu | Leu | Leu | Leu | Ser | Gly |
| 1 | | | | 5 | | | | | 10 | | | | | 15 | | | | | 20 |
| Cys | Leu | Leu | Ala | Ala | Ala | Arg | Arg | Glu | Lys | Gly | Ala | Ala | Ser | Asn | Val | Ala | Glu | Pro | Val |
| 21 | | | | 25 | | | | | 30 | | | | | 35 | | | | | 40 |
| Pro | Gly | Pro | Thr | Gly | Gly | Ser | Ser | Gly | Arg | Phe | Leu | Ser | Pro | Glu | Gln | His | Ala | Cys | Ser |
| 41 | | | | 45 | | | | | 50 | | | | | 55 | | | | | 60 |
| Trp | Gln | Leu | Leu | Leu | Pro | Ala | Pro | Glu | Ala | Ala | Ala | Gly | Ser | Glu | Leu | Ala | Leu | Arg | Cys |
| 61 | | | | 65 | | | | | 70 | | | | | 75 | | | | | 80 |
| Gln | Ser | Pro | Asp | Gly | Ala | Arg | His | Gln | Cys | Ala | Tyr | Arg | Gly | His | Pro | Glu | Arg | Cys | Ala |
| 81 | | | | 85 | | | | | 90 | | | | | 95 | | | | | 100 |
| Ala | Tyr | Ala | Ala | Arg | Arg | Ala | His | Phe | Trp | Lys | Gln | Val | Leu | Gly | Gly | Leu | Arg | Lys | Lys |
| 101 | | | | 105 | | | | | 110 | | | | | 115 | | | | | 120 |
| Arg | Arg | Pro | Cys | His | Asp | Pro | Ala | Pro | Leu | Gln | Ala | Arg | Leu | Cys | Ala | Gly | Lys | Lys | Gly |
| 121 | | | | 125 | | | | | 130 | | | | | 135 | | | | | 140 |
| His | Gly | Ala | Glu | Leu | Arg | Leu | Val | Pro | Arg | Ala | Ser | Pro | Pro | Ala | Arg | Pro | Thr | Val | Ala |
| 141 | | | | 145 | | | | | 150 | | | | | 155 | | | | | 160 |
| Gly | Phe | Ala | Gly | Glu | Ser | Lys | Pro | Arg | Ala | Arg | Asn | Arg | Gly | Arg | Thr | Arg | Glu | Arg | Ala |
| 161 | | | | 165 | | | | | 170 | | | | | 175 | | | | | 180 |
| Ser | Gly | Pro | Ala | Ala | Gly | Thr | Pro | Pro | Pro | Gln | Ser | Ala | Pro | Pro | Lys | Glu | Asn | Pro | Ser |
| 181 | | | | 185 | | | | | 190 | | | | | 195 | | | | | 200 |
| Glu | Arg | Lys | Thr | Asn | Glu | Gly | Lys | Arg | Lys | Ala | Ala | Leu | Val | Pro | Asn | Glu | Glu | Arg | Pro |
| 201 | | | | 205 | | | | | 210 | | | | | 215 | | | | | 220 |
| Met | Gly | Thr | Gly | Pro | Asp | Pro | Asp | Gly | Leu | Asp | Gly | Asn | Ala | Glu | Leu | Thr | Glu | Thr | Tyr |
| 221 | | | | 225 | | | | | 230 | | | | | 235 | | | | | 240 |
| Cys | Ala | Glu | Lys | Trp | His | Ser | Leu | Cys | Asn | Phe | Phe | Val | Asn | Phe | Trp | Asn | Gly | | |
| 241 | | | | 245 | | | | | 250 | | | | | 255 | | | | | 260 |

Figure 1

NBP158 AND USES THEREOF

CROSS REFERENCE OF RELATED APPLICATION

The present disclosure is the national phase of International Application No. PCT/CN2014/093344, titled "NBP158 AND USES THEREOF", filed on Dec. 9, 2014, which is incorporated herein by reference in entirety.

SEQUENCE LISTING

A Sequence Listing is being submitted as an ASCII text file via EFS-Web, file name "170025-FSU-PERSON-Revised-Sequence-Listing.txt", size 8234 bytes, created on Feb. 24, 2020, the content of which is incorporated herein by reference.

FIELD

The present invention relates to nucleic acid molecules encoding the N-terminal 158 amino acids of secreted human Fibroblast Growth Factor Binding Protein 3 (NBP158), a pharmaceutical compositions comprising the NBP158 protein, and methods for treating metabolic disorders and conditions using such nucleic acids, proteins, or pharmaceutical compositions.

BACKGROUND

Epidemics, Pathophysiology and Treatment of Diabetes Mellitus

Diabetic Mellitus (DM) is a group of diseases marked by high levels of blood glucose resulting from defects in insulin production, insulin action, or both. DM can lead to serious complications and premature death. In 2010, DM affects 25.8 million people of all ages in U.S., including 18.8 million diagnosed and 7.0 million undiagnosed. Based on fasting glucose or hemoglobin A1C levels, 50 percent of adults aged 65 or older have prediabetes. DM is the leading cause of kidney failure, nontraumatic lower-limb amputations, and new cases of blindness among adults, a major cause of heart diseases and stroke, and the seventh leading cause of death in the United States.

Type 1 DM, or insulin-dependent diabetes mellitus (IDDM), develops when the body's immune system destroys pancreatic cells, the only cells that make insulin. Type 2 DM, or non-insulin-dependent diabetes mellitus (NIDDM), begins as insulin resistance, a disorder in which the cells do not use insulin properly. As the need for insulin rises, the pancreas gradually loses its ability to produce insulin. Gestational diabetes is a form of glucose intolerance diagnosed during pregnancy. Other types of DM result from specific genetic conditions, surgery, medications, infections, pancreatic disease and other illness.

Current treatment and management for DM include patient education, self-care practices, diet, insulin and oral medications to lower blood glucose level. Patients with type 1 DM must have insulin injected. For type 2 DM, prevention of complications by glucose control, blood pressure control, blood lipids control, and preventive care for eyes, feet and kidneys are very important. For patients with early stage type 2 DM, a healthy meal plan and exercise program, losing excess weight, and taking oral medications can put their blood glucose level under control. But for those with late stage type 2 DM, both oral medications and insulin are necessary. A high dose of insulin represses the production of endogenous insulin by pancreas, and it may not lower the blood glucose level since insulin resistance is present in many patients with type 2 DM.

Pathophysiological studies reveal that increased insulin resistance and inadequate insulin secretion are major underlying causes of the hyperglycemic state in type 2 diabetes. Insulin resistance is typically present before diagnosis, manifested as suppressed glucose production in the liver in response to insulin and diminished stimulation of glucose transport into muscle and adipose tissue. Euglycemia, however, can be maintained as long as beta cells secrete higher amounts of insulin. Eventually, insulin levels decline because of the decreased number of beta cells and their diminished secretory capacity.

The overall goal of glycemic management is to minimize long-term complications while avoiding severe hypoglycemic events. The target of glycemic control is to keep glycated hemoglobin level less than 7.0%. The currently available oral hypoglycemic drugs include agents that improve insulin sensitivity, such as Metformin, Thiazolidinediones (pioglitazone and rosiglitazone); agents that increase circulating insulin levels, such as Sulfonylureas (e.g., glipizide, glyburide, etc.), Metlitinides (e.g., repaglinide, nateglinide), GLP-1-receptor agonists (e.g., exenatide, liraglutide), and Dipeptidyl peptidase IV (DPP-IV) inhibitors (e.g., sitagliptin, saxagliptin); other agents, such as Alpha-glucosidase inhibitors (e.g., Acarbose, Meglitol), bile acid sequestrant (e.g., colesevelam), dopamine agonist (e.g., bromocriptine), amylin mimetic (e.g., pramlintide). In patients with clinically significant hyperglycemia (blood glucose level, >300 mg/dl or 16.7 mmol/1; glycated hemoglobin level, >10%), insulin therapy should be initiated. Hypoglycemia and weight gain are the major concerns for long-term use of insulin.

In summary, glycemic control in patients with type 2 DM is critical, however, the current medications, both oral and injectable, are far from the ultimate option. New hypoglycemic agents through distinct mechanisms are needed to better treat or even cure type 2 DM.

Physiology and Biochemistry of FGFBP3

FGFBP3 is a member of the FGF Binding Protein family (FGFBP1, -2, and -3). Human FGFBP3 precursor (Accession NP_689642, RefSeq NM_152429.4, CCDS ID7418.1) consists of 258 amino acids with a signal peptide of 26 residue-long (1-26 amino acids) and a secreted peptide of 232 residue-long (27-258 amino acids) in FIG. 1 (SEQ ID NO: 1). DNA encoding human FGFBP3 may be obtained from a cDNA library prepared from many tissues, such as brain, colon, liver, lung, etc., which possess the FGFBP3 mRNA and express it at a detectable level.

Paracrine/autocrine factors, such as FGF1 and -2, are sequestered to the extracellular matrix, as well as the cell surface, by heparan sulfate proteoglycans (HSPGs) due to a high binding affinity Endocrine factors, such as FGF19, -21, and -23, can travel a long distance in the circulation due to a low binding affinity. FGFBP family proteins (FGFBP1, -2, and -3) do not activate FGF signaling pathway in vitro or in vivo if they were administered without exogenous FGFs. In the presence of exogenous FGFs, FGFBP proteins significantly enhance the FGF signaling. FGFBP3 binds to paracrine/autocrine FGFs, such as FGF1 and -2, or endocrine FGFs, such as FGF19, -21 and -23. Since FGFs and their receptors are involved in the proliferation and progression of many cancer cell lines and primary tumors, the mitogenic potential is one major concern for FGFBP3 as a long-term administered drug. For example, FGFBP3 binds with high affinity to FGF19 that induces the development of hepatocellular carcinoma (HCC) in transgenic mice expressing human FGF19 in skeletal muscle. Recently, FGF19 neutralizing antibodies have been used to prevent HCC development in FGF19 transgenic mice partly mediated by suppressing β-catenin signaling, which further confirms the role of FGF19 in HCC progression.

Fibroblast growth factor binding protein 3 (FGFBP3) also binds to heparin in vitro with high affinity by itself, but with a low affinity in the presence of FGF2. However, the binding affinity of FGFBP3 to HSPGs in vivo is unknown. Recent studies suggest that FGFBP3 may play a functional role both locally and systemically. In chicken embryos, FGFBP3 is found to increase vascular permeability in the brain via the activation of paracrine/autocrine FGF signaling; in knockout mouse model, FGFBP3 plays a critical role in the regulation of anxiety-related behaviors through distinct signaling pathways. Preliminary phenotype data also provide evidence of decreased lean body mass in FGFBP3 deficient (−/−) mice, which suggests that FGFBP3 may be involved in the regulation of fuel metabolism in an endocrine manner.

SUMMARY

The present invention provides novel therapeutic proteins and novel regimens for treatment of Metabolic Disorders and conditions including Diabetes Mellitus and obesity. The therapeutic proteins include secreted human Fibroblast Growth Factor Binding Protein 3 (FGFBP3) and the N-terminal 158 amino acids of secreted FGFBP3 (NBP158).

In one embodiment, the invention provides a synthesized nucleic acid molecule comprising DNA encoding a human FGFBP3 protein mutant, NBP158.

In one aspect, the synthesized nucleic acid comprises DNA that is at least 75%, 80%, 85%, 86%, 87%, 88%, 89%, 90%, 91%, 92%, 93%, 94%, 95%, 96%, 97%, 98% or 99% identical to (a) a DNA molecule encoding the N-terminal 158 amino acids (NBP158) of human FGFBP3 polypeptide having the sequence of amino acid residues from 1 to about 184 or from 27 to about 184, inclusive of FIG. 1 (SEQ ID NO:1), or (b) the complement of the DNA molecule of (a).

In a further aspect, the invention provides a vector comprising DNA encoding NBP158 or its variants. The vector may comprise any of the synthesized nucleic acid molecules hereinabove defined. A host cell comprising such a vector is also provided. By way of example, the host cells may be CHO cells, *E. coli*, or yeast. A process for producing NBP158 polypeptides is further provided and comprises culturing host cells under conditions suitable for expression of NBP158 and recovering NBP158 from the cell culture.

In a still further aspect, the invention provides recombinant NBP158 polypeptide encoded by any of the synthesized nucleic acid sequences hereinabove defined. NBP158 polypeptide consists of a peptide with an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of amino acid residues (a) from 1 to about 184 or (b) from 27 to about 184, inclusive of FIG. 1 (SEQ ID NO:1).

In another embodiment, the invention provides a composition comprising a human FGFBP3 polypeptide, or a human FGFBP3 mutant polypeptide as hereinabove defined (NBP158), in combination with a pharmaceutically acceptable carrier. In one aspect, the composition comprises a therapeutically effective amount of a FGFBP3 or NBP158. Preferably, the composition is sterile.

In a further embodiment, the invention provides a method of treating Diabetes Mellitus in a mammal, comprising systemically delivering a pharmaceutical composition as hereinabove defined into a mammal, intraperitoneally, intravenously, subcutaneously or intramuscularly.

In a still further embodiment, the invention provides a method of treating Obesity in a mammal, comprising systemically delivering a pharmaceutical composition as hereinabove defined into a mammal, intraperitoneally, intravenously, subcutaneously or intramuscularly.

In yet another embodiment, the invention concerns a method for treating dyslipidemia and complications of metabolic disorders, comprising systemically delivering a pharmaceutical composition as hereinabove defined into a mammal, intraperitoneally, intravenously, subcutaneously or intramuscularly.

BRIEF DESCRIPTION OF THE DRAWINGS

FIG. 1, Amino Acid Sequence of Human FGFBP3 (SEQ ID NO: 1).

DETAILED DESCRIPTION OF EMBODIMENTS

Figure 2:
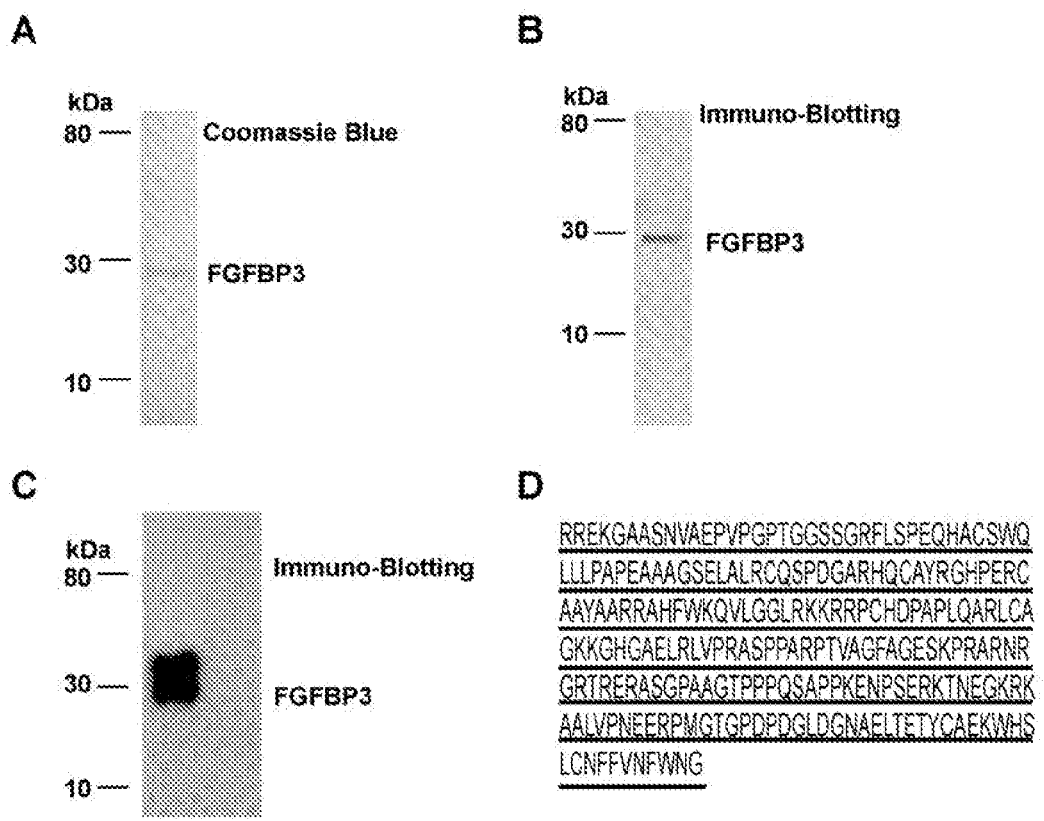
FIG. 2, Human FGFBP3 protein (untagged) expression in CHO cells. A,B, The secreted human FGFBP3 (amino acid 27-258 of SEQ ID NO: 1, i.e., SEQ ID NO: 2) in supernatants from CHO cells transfected with a human FGFBP3 expression vector (for 72 h) is shown by Coomassie Blue staining (A) and detected by immunoblotting (IB) for FGFBP3 (B). C, CHO Cell lysates are loaded and immunoblotting for FGFBP3 is performed to detect both FGFBP3 precursors and secreted FGFBP3 peptide. D, The indicated protein sample in panel A is analyzed by mass spectrometry and 100% sequence (shown as underlined) of secreted human FGFBP3 peptides are identified by LC/MS.
Figure 3:
FIG. 3, Amino acid sequences and disulfide bond bridges of synthesized 66-residual-long C-terminal tail of human BP3 (CBD66, amino acid 193-258 of SEQ ID NO: 1, i.e., SEQ ID NO:3).

The present invention provides compositions and methods for treatment of metabolic disorders and conditions, such as Diabetes Mellitus (DM) and obesity. In one embodiment, the invention uses FGFBP3 protein or FGFBP3 mutant proteins, including human FGFBP3 and NBP158, to achieve therapeutic benefits for DM. The invention provides novel polypeptides, nucleic acid molecules, vectors and host cells. The invention provides methods for using novel polypeptides to reduce the fasting glucose and improve the glucose tolerance in DM. The invention also provides the optimized dosage, duration, and administration route of the treatment of DM and obesity.

1. Definitions

The terms "NBP158 polypeptide", "NBP158 protein" and "NBP158" when used herein encompass polypeptides that are at least 75%, 80%, 85%, 86%, 87%, 88%, 89%, 90%, 91%, 92%, 93%, 94%, 95%, 96%, 97%, 98% or 99% identical to the amino acid sequence of residues 27 to 184 of SEQ ID NO: 1 (i.e., SEQ ID NO: 4) or 1 to 184 of SEQ ID NO: 1 (i.e., SEQ ID NO: 5). The NBP158 may be prepared by recombinant and/or synthetic methods.

"NBP158 mutant" means anything other than a native sequence NBP158 which is an active NBP158, as defined below, having at least about 80% amino acid sequence identity with the amino acid sequence of residues 27 to 184 or 1 to 184 of the FGFBP3 polypeptide having the deduced amino acid sequence shown in FIG. 1 (SEQ ID NO: 1). Such FGFBP3 mutants include, for instance, NBP158 polypeptides wherein one or more amino acid residues are added, or deleted, at the N- or C-terminus, as well as within one or more internal domains, of the sequence of residues 27 to 184 or 1 to 184 of FIG. 1 (SEQ ID NO: 1).

A "native sequence FGFBP3" comprises a polypeptide having the same amino acid sequence as a FGFBP3 derived from nature. Such native sequence FGFBP3 can be isolated from nature or can be produced by recombinant and/or synthetic means. The term "native sequence FGFBP3" specifically encompasses naturally-occurring truncated or secreted forms (e.g., an extracellular domain sequence), naturally-occurring variant forms (e.g., alternatively spliced forms) and naturally-occurring allelic variants of the FGFBP3. In one embodiment of the invention, the native sequence FGFBP3 is a mature or full-length native sequence FGFBP3 comprising amino acids 27 to 258 (alternatively 1 to 258) of FIG. 1 (SEQ ID NO: 1).

The terms "polypeptide" and "protein" are used interchangeably and refer to a compound made up of a single chain of amino acid residues linked by peptide bonds. A polypeptide or protein can, but need not, comprise non-naturally occurring amino acids and amino acid derivatives. A non-limiting lists of examples of non-naturally occurring amino acids that can be inserted into a protein or polypeptide (including chimeric polypeptides disclosed herein) include amino acids, homoamino acids, cyclic amino acids and amino acids with derivatized side chains. Examples include (in the L-form or D-form; abbreviated as in parentheses): para-acetyl-phenylalanine, para-azido-phenylalanine, para-bromo-phenylalanine, para-iodo-phenylalanine and para-ethynyl-phenylalanine, citrulline (Cit), homocitrulline (hCit), Na-methylcitrulline (NMeCit), Na-methylhomocitrulline (Na-MeHoCit), ornithine (Om), Na-Methylornithine (Na-MeOrn or NMeOrn), sarcosine (Sar), homolysine (hLys or hK), homoarginine (hArg or hR), homoglutamine (hQ), Na-methylarginine (NMeR), Na-methylleucine (Na-MeL or NMeL), N-methylhomolysine (NMeHoK), Na-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nai), 3-(2-naphthyl)alanine (2-Nai), 1,2,3,4-tetrahydroisoquinoline (Tic), 2-indanylglycine (Igi), para-iodophenylalanine (pi-Phe), para-aminophenylalanine (4AmP or 4-Amino-Phe), 4-guanidino phenylalanine (Guf), glycyllysine (abbreviated "K(NE-glycyl)" or "K(glycyl)" or "K(gly)"), nitrophenylala-nine (nitrophe), aminophenylalanine (aminophe or Amino-Phe), benzylphenylalanine (benzylphe), y-carboxy-glutamic acid (y-carboxyglu), hydroxyproline (hydroxypro), p-car-boxyl-phenylalanine (Cpa), a-aminoadipic acid (Aad), Na-methyl valine (NMeVal), N-a-methyl leucine (NMeLeu), Na-methylnorleucine (NMeN!e), cyclopen-tylglycine (Cpg), cyclohexylglycine (Chg), acetylarginine (acetylarg), a, -di-aminopropionoic acid (Dpr), a,y-di-aminobutyric acid (Dab), diaminopropionic acid (Dap), cyclohexylalanine (Cha), 4-methyl-phenylalanine (MePhe), -diphenyl-alanine (Bi-PhA), aminobutyric acid (Abu), 4-phenyl-phenylalanine (or biphenylalanine; 4Bip), a-amino-isobutyric acid (Aib), beta-alanine, beta-aminopro-pionic acid, piperidinic acid, ami-nocaprioic acid, amino-heptanoic acid, aminopimelic acid, desmosine, diaminopimelic acid, N-ethylglycine, N-ethylas-pargine, hydroxylysine, allo-hydroxylysine, isodesmosine, allo-iso-leucine, N-methylglycine, N-methylisoleucine, N-methyl-valine, 4-hydroxyproline (Hyp), y-carboxy-glutamate, e-N, N,N-trimethyllysine, E-N-acetyllysine, 0-phosphoserine, N-acetylserine, N-formylmethionine, 3-methylhistidine, 5-hydroxylysine, w-methylarginine, 4-Amino-0-Phthalic Acid (4APA), and other similar amino acids, and derivatized forms of any of those specifically listed.

"Percent (%) amino acid sequence identity" with respect to the NBP158 sequences identified herein is defined as the percentage of amino acid residues in a candidate sequence that are identical with the amino acid residues in the NBP158 sequence, after aligning the sequences and intro-ducing gaps, if necessary, to achieve the maximum percent sequence identity, and not considering any conservative substitutions as part of the sequence identity. The % identity values used herein are generated by DELTA-BLAST which was obtained from NCBI. DELTA-BLAST uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by DELTA-BLAST to maximize the alignment score are ignored).

In a similar manner, "percent (%) nucleic acid sequence identity" with respect to the coding sequence of the NBP158 polypeptides identified herein is defined as the percentage of nucleotide residues in a candidate sequence that are identical with the nucleotide residues in the NBP158 coding sequence. The identity values used herein were generated by BLASTN set to the default parameters, with overlap span and overlap fraction set to 1 and 0.125, respectively.

"Isolated," when used to describe the various polypep-tides disclosed herein, means polypeptide that has been identified and separated and/or recovered from a component of its natural environment. Contaminant components of its natural environment are materials that would typically inter-fere with diagnostic or therapeutic uses for the polypeptide, and may include enzymes, hormones, and other proteina-ceous or non-proteinaceous solutes. In preferred embodi-ments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the FGFBP3 natural environment will not be present. Ordinarily, however, isolated polypeptide will be prepared by at least one purification step.

An "isolated" nucleic acid molecule encoding a FGFBP3 polypeptide is a nucleic acid molecule that is identified and separated from at least one contaminant nucleic acid mol-ecule with which it is ordinarily associated in the natural source of the FGFBP3-encoding nucleic acid. An isolated FGFBP3-encoding nucleic acid molecule is other than in the form or setting in which it is found in nature. Isolated FGFBP3-encoding nucleic acid molecules therefore are dis-tinguished from the FGFBP3-encoding nucleic acid mol-ecule as it exists in natural cells. However, an isolated nucleic acid molecule encoding a FGFBP3 polypeptide includes FGFBP3-encoding nucleic acid molecules con-tained in cells that ordinarily express FGFBP3 where, for example, the nucleic acid molecule is in a chromosomal location different from that of natural cells.

As used herein, the term "vector" is used to refer to any molecule (e.g., nucleic acid, plasmid, or virus) used to transfer coding information to a host cell.

As used herein, the term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate trans-lation. Generally, "operably linked" means that the DNA sequences being linked are contiguous, and, in the case of a secretory leader, contiguous and in reading phase. However, enhancers do not have to be contiguous. Linking is accom-plished by ligation at convenient restriction sites. If such sites do not exist, the synthetic oligonucleotide adaptors or linkers are used in accordance with conventional practice.

The term "epitope tagged" when used herein refers to a chimeric polypeptide comprising a NBP158 polypeptide fused to a "tag polypeptide". Suitable tag polypeptides generally have at least six amino acid residues and usually between about 8 and 50 amino acid residues (preferably, between about 10 and 20 amino acid residues).

As used herein, the term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

"Active" or "activity" for the purposes herein refers to form(s) of NBP158 which retain the biologic and/or immunologic activities of recombinant or synthetic NBP158. Preferably, activity refers to the ability to improve glucose metabolism or reduce body weight.

"Biological activity" in the context of a protein or another molecule that can be identified by the animal study is used to refer to the ability of such protein or other molecules to change the in vivo physiological parameters, such as blood glucose, blood pressure, temperature, body weight, etc.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In Diabetes Mellitus treatment, a therapeutic agent may directly decrease the fasting plasma glucose level or improve the glucose tolerance.

As used herein, the terms "effective amount" and "therapeutically effective amount" each refer to the amount of a chimeric polypeptide disclosed herein used to support an observable level of one or more biological activities of NBP158 or its mutant polypeptides, such as the ability to lower blood glucose, insulin, triglyceride, or cholesterol levels; reduce body weight; or improve glucose tolerance, energy expenditure, or insulin sensitivity in a human or non-human subject.

"Mammal" for purposes of treatment refers to any animal classified as a mammal, including humans, domestic and farm animals, and zoo, sports, or pet animals, such as dogs, horses, cats, cattle, etc. Preferably, the mammal is human.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

2. Compositions of the Invention a. The N-Terminal 158 Amino Acid Residues of Human FGFBP3 Secreted Polypeptide (NBP158)

The present invention provides a synthetic nucleotide sequence encoding polypeptide referred to in the present application as NBP158. In particular, cDNA encoding amino acids from 1 to 184 of full length FGFBP3 polypeptide (SEQ ID NO: 1), i.e., SEQ ID NO: 5 has been synthesized and optimized, as disclosed in further detail in the Examples below. The open reading frame of 184 amino acids is subcloned into a commercially available vector. NBP158 is produced as a recombinant protein without C-terminal epitope tags. The untagged NBP158 protein is secreted from plasmid transfected CHO cells, encoding amino acids from 27 to 184 of full length FGFBP3 polypeptide (SEQ ID NO: 1), i.e., SEQ ID NO: 4.

b. NBP158 Mutant Polypeptide

In addition to the full-length or secreted sequence NBP158 polypeptides described herein, it is contemplated that NBP158 mutants can be prepared. NBP158 mutants can be prepared by introducing appropriate nucleotide changes into the NBP158 DNA, and/or by synthesis of the desired NBP158 mutant polypeptide as described in the examples below. Those skilled in the art will appreciate that amino acid changes may alter post-translational processes of the NBP158, such as changing the number or position of glycosylation sites or altering the phosphorylation sites.

Variations in the full-length sequence NBP158 or in various domains of the NBP158 described herein, can be made, for example, using any of the techniques and guidelines for conservative and non-conservative mutations set forth. Variations may be a substitution, deletion or insertion of one or more codons encoding the NBP158 that results in a change in the amino acid sequence of the NBP158 as compared with the amino acid residues from 1 to about 184 of SEQ ID NO: 1 (i.e., SEQ ID NO: 5) or from 27 to about 184 of SEQ ID NO: 1 (i.e. SEQ ID NO: 4). Optionally the variation is by substitution of at least one amino acid with any other amino acid in one or more of the domains of the NBP158. Guidance in determining which amino acid residue may be inserted, substituted or deleted without adversely affecting the desired activity may be found by comparing the sequence of the NBP158 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay.

The mutations can be made using methods known in the art such as oligonucleotide-mediated (site-directed) mutagenesis, alanine scanning, and PCR mutagenesis. Site-directed mutagenesis, cassette mutagenesis, restriction selection mutagenesis or other known techniques can be performed on the cloned DNA to produce the NBP158 mutant. DNA scanning amino acid analysis can also be employed to identify one or more amino acids along a contiguous sequence. Among the preferred scanning, amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions. If alanine substitution does not yield adequate amounts of variant, an isosteric amino acid can be used.

c. Expression and Detection of Polypeptides

The description below relates primarily to production of NBP158 by culturing cells transformed or transfected with a vector containing NBP158 nucleic acid. It is, of course, contemplated that alternative methods, which are well known in the art, may be employed to prepare NBP158. For instance, the NBP158 sequence, or portions thereof, may be produced by direct peptide synthesis using solid phase techniques. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the NBP158 may be chemically synthesized separately and combined using chemical or enzymatic methods to produce the full-length NBP158.

Host cells are transfected or transformed with expression or cloning vectors described herein for NBP158 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, CaPO4 and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983). For mammalian cells without such cell walls, the calcium phosphate precipitation method of Graham and van der Eb, Virology, 52:456-457 (1978) can be employed. General aspects of mammalian cell host system transformations have been described. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g. polybrene, polyornithine, may also be used. For various techniques for transforming mammalian cells, see Keown et al., *Methods in Enzymology*, 185: 527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). In addition to prokaryotes, eukaryotic microbes such as filamentous fungi or yeast are suitable cloning or expression hosts for FGFBP3-encoding vectors. *Saccharomyces cerevisiae* is a commonly used lower eukaryotic host microorganism.

Suitable host cells for the expression of glycosylated NBP158 are derived from multicellular organisms. Examples of invertebrate cells include insect cells such as *Drosophila* S2 and *Spodoptera* SP9, as well as plant cells. Examples of useful mammalian host cell lines include Chinese hamster ovary (CHO) and COS cells. More specific examples include monkey kidney CVI line transformed by SV40 (COS-7, ATCC CRL 1651); human embryonic kidney line (293 or 293 cells subcloned for growth in suspension culture, Graham et al., *J. Gen Viral.*, 36:59 (1977)); Chinese hamster ovary cells/-DHFR; mouse sertoli cells (TM4); human lung cells (W138, ATCC CCL 75); human liver cells (Hep G2, HB 8065); and mouse mammary tumor (MMT060562, ATCC CCLS 1). The selection of the appropriate host cell is deemed to be within the skill in the art.

The nucleic acid (e.g., cDNA or genomic DNA) encoding NBP158 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The NBP158 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the NBP158-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces* a-factor leaders), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2fA plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An example of suitable selectable markers for mammalian cells are those that enable the identification of cells competent to take up the FGFBP3-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the NBP158-encoding nucleic acid sequence to direct mRNA synthesis. Promoters recognized by a variety of potential host cells are well known. Promoters suitable for use with prokaryotic hosts include the lactamase and lactose promoter systems, alkaline phosphatase, a tryptophan (trp) promoter system, and hybrid promoters such as the tac promoter. Promoters for use in bacterial systems also will contain a Shine-Dalgarno (S.D.) sequence operably linked to the DNA encoding NBP158.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

NBP158 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the NBP158 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the FGFBP3 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding FGFBP3.

Still other methods, vectors, and host cells suitable for adaptation to the synthesis of NBP158 in recombinant vertebrate cell culture are described in Gething et al., *Nature,* 293:620-625 (1981); Mantei et al., *Nature,* 281:40-46 (1979); EP 117,060; and EP 117,058.

Gene amplification and/or expression may be measured in a sample directly, for example, by conventional Southern blotting, Northern blotting to quantitate the transcription of mRNA, dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against the full sequence NBP158 polypeptide or against a synthetic peptide based on the DNA sequences provided herein or against exogenous sequence fused to NBP158 DNA and encoding a specific antibody epitope.

d. Purification of Polypeptides

Forms of NBP158 may be recovered from culture medium or from host cell lysates. If membrane-bound, it can be released from the membrane using a suitable detergent solution (e.g. Triton-X 100) or by enzymatic cleavage. Cells employed in expression of NBP158 can be disrupted by various physical or chemical means, such as freeze-thaw cycling, sonication, mechanical disruption, or cell lysing agents.

It may be desired to purify NBP158 from recombinant cell proteins or polypeptides. The following procedures are exemplary of suitable purification procedures: by fractionation on an ion-exchange column; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; protein A Sepharose columns to remove contaminants such as IgG; Heparin columns to purify with high binding affinity NBP158; and metal chelating columns to bind epitope-tagged forms of the NBP158. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular NBP158 produced. 3. Uses of NBP158 and NBP158 Mutants a. Pharmaceutical Compositions NBP158 polypeptide, as well as NBP158 mutants, can be administered for the treatment of metabolic disorders and conditions, including DM and obesity in the form of pharmaceutical compositions.

Therapeutic formulations of the polypeptide are prepared for storage as lyophilized formulations or aqueous solutions by mixing the polypeptide having the desired degree of purity with optional "pharmaceutically acceptable" or "physiologically acceptable" carriers, excipients or stabilizers typically employed in the art (all of which are termed "excipients"). For example, buffering agents, stabilizing agents, preservatives, isotonifiers, nonionic detergents, antioxidants and other miscellaneous additives. (See Remington's Pharmaceutical Sciences, 16th edition (or later), A Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof. For example, citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris may be employed.

Preservatives are added to retard microbial growth, and are added in amounts ranging from 0.2%-1% (w/v). Suitable preservatives for use with the present invention include phenol, benzyl alcohol, metacresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5%, taking into account the relative amounts of the other ingredients.

Stabilizers refer to a broad category of excipients that can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, amonothioglycerol and sodium thiosulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers can be present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml. Additional miscellaneous excipients include bulking agents, (e.g. starch), chelating agents (e.g. EDTA), antioxidants (e.g., ascorbic acid, methionine, vitamin E), and cosolvents.

The formulations herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coaservation techniques or by interfacial polymerization, for example, hydroxylmethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition (or later), A Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semipermeable matrices of solid hydrophobic polymers containing the FGFBP3 polypeptide mutants, which matrices are in the form of shaped articles, e.g. films or microcapsules. Examples of sustained-release matrices include polyesters, hydrogels, for example, poly(2-hydroxyethylmethacrylate), or poly(vinylalcohol), polylactides, copolymers of L-glutamic acid and ethyl-L-glutamate, nondegradable ethylenevinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Non-protein compounds identified by the screening assays of the present invention can be formulated in an analogous manner, using standard techniques well known in the art.

b. Methods of Treatment

The agents of the present invention, e.g. NBP158 protein or NBP158 mutants, are administered to a mammal, preferably a human, in accord with known methods, such as intravenous administration as a bolus or by continuous infusion over a period of time, by intramuscular, intraperitoneal, intracerebrospinal, subcutaneous, intraarticular, intrasynovial, intrathecal, oral, topical, or inhalation routes. Intravenous administration of the polypeptide is preferred. For the prevention or treatment of disease, the appropriate dosage of an agent, e.g., an protein herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

The amount of therapeutic polypeptide or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local therapeutic agent concentration of between about 5 and 20 ng/ml, and, preferably, between about 10 and 20 ng/ml.

The dosing schedule for subcutaneous administration may vary form once a month to daily depending on a number of clinical factors, including the type of disease, severity of disease, and the subject's sensitivity to the therapeutic agent. For example, depending on the type and severity of the disease, about 500 ng/kg to 100 mg/kg (i.e. 0.0005-100 mg/kg) of protein is an initial candidate dosage for administration to the patient, whether, for example, by one or more separate administrations, or by continuous infusion. A typical daily dosage might range from about 1 µg/kg to 20 mg/kg or more, depending on the factors mentioned above. For repeated administrations over several days or longer, depending on the condition, the treatment is sustained until a desired suppression of disease symptoms occurs. However, other dosage regimens may be useful. Conventional techniques and assays easily monitor the progress of this therapy.

Figure 7:
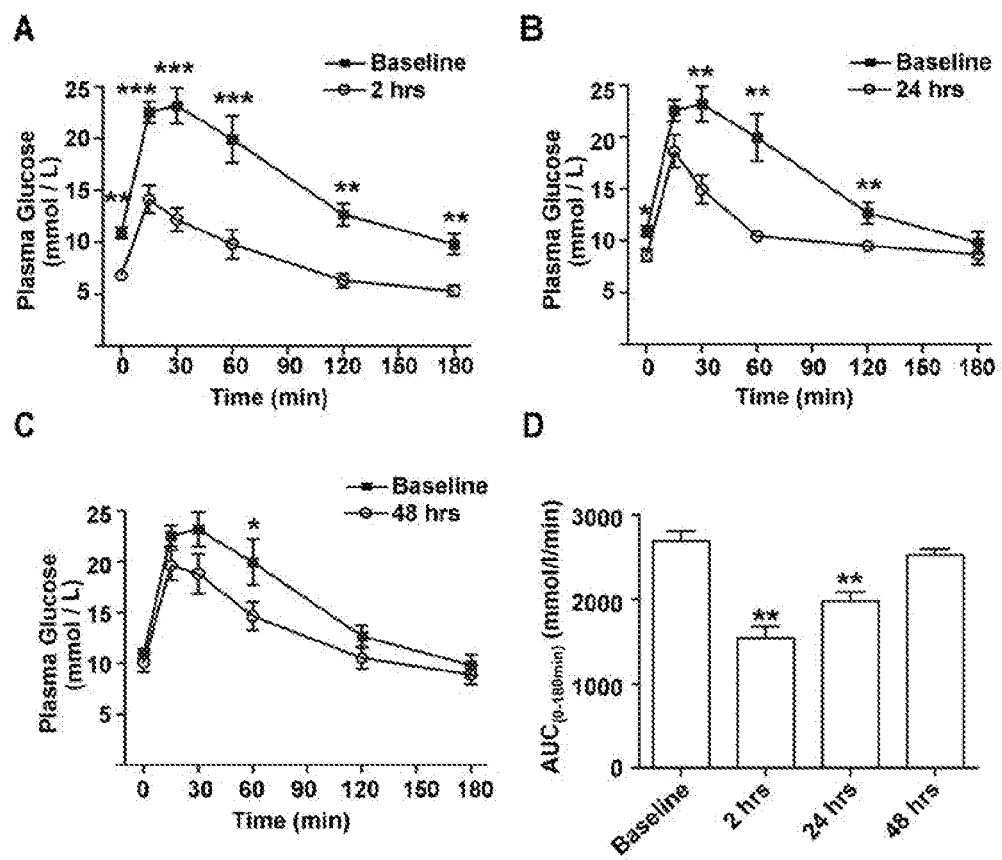
FIG. 7, Time course of single NBP158 treatment on glucose metabolism in ob/ob mice. A, 2 hrs after a single NBP158 injection, the glucose tolerance is significantly improved at 60 and 90 min before and after treatment (n=6). B, 24 hrs after a single NBP158 treatment, the fasting glucose is not decreased, but a significant difference is shown at 30 and 60 min (n=6). C, 48 hrs after a single NBP158 treatment, a significant difference is shown at 120 min (n=6) (*, p<0.05; , p<0.01; *, p<0.001). D, Improvement of glucose metabolism in ob/ob mice at 2 hours (n=8), 24 hours (n=6), and 48 hours (n=5) after single NBP158 treatment. (*, p<0.05; , p<0.01; *, p<0.001). Symbols (*, , and *) indicate significant differences in plasma glucose level before (baseline) and after NBP158 treatment.

In one embodiment, NBP158 alone has immediate effects on the glucose tolerance in fasted ob/ob mice. As shown in FIG. 7A, a single dose of FGFBP3 alone significantly decreased the serum glucose level at 15, 30, 60, 120, and 180 min after 2 hrs treatment. The maximal pharmacological effect occurs at 2 hrs after a single dose of the combination regimen, lasts for at least 24 hours, and comes back to baseline after 2 days.

In a still further embodiment, NBP158 improves the glucose tolerance in diet-induced-obesity (DOO) mice, a clinically relevant diabetic animal model. First, the single treatment with NBP158 (0.5 mg/kg) significantly lowers the fasting glucose level and improves glucose tolerance, but a single dose of CBD66 shows no effect even at much higher dosage (from 1 mg/kg to 5 mg/kg).

As can be appreciated by one of ordinary skill, optimal dosages and desired drug concentrations of pharmaceutical compositions of the present invention may vary depending on the particular use envisioned. The determination of the appropriate dosage or route of administration is well within the skill of an artisan of ordinary skill in the art. Animal experiments provide reliable guidance for the determination of effective doses for human therapy. Interspecies scaling of effective doses can be performed following the principles laid down by Mordenti, J. and Chappell, W., "The use of interspecies scaling in toxicokinetics", *Toxicokinetics and New Drug Development*, Yacobi et al., Eds, Pergamon Press, New York 1989, pp. 42-96.

In summary, NBP158 polypeptide, the N-terminal 158 amino acids of human secreted FGFBP3, dramatically reduces the plasma glucose level in a dose-dependent manner, with a rapid onset (<2 hrs) and long duration (>24 hrs). Human secreted FGFBP3 protein improves the glucose metabolism not through its C-terminal FGF-binding domain, CBD66. The glucose-lowering effect of FGFBP3 is independent of FGF signaling. Since NBP158 doesn't bind to FGFs, we conclude that NBP158 treatment is unlikely to induce development of cancer, e.g., hepatocellular carcinoma (HCC). Therefore, NBP158 is a very safe and promising therapeutic peptide for metabolic disorders, including DM and obesity.

EXAMPLES

Example 1: Amino Acid Sequences of Human FGFBP3 and the N-Terminal 158 Amino Acids of Secreted Human FGFBP3 (NBP158)

Human fibroblast growth factor-binding protein 3 precursor (FGFBP3, accession NP_689642, RefSeq NM_152429.4, CCDS ID7418.1) consists of 258 amino acids with a signal peptide of 26 residue-long (amino acid 1-26) and a secreted peptide of 232 residue-long (amino acid 27-258) in FIG. 1 (SEQ ID NO: 1). A BLAST search with human FGFBP3 (NP_689642.3) shows 57.6% identity and 67.6% similarity to mouse FGFBP3 (NP_114156) by EMBOSS Water software. Hydropathy plot analysis reveals one strongly hydrophobic region at the N terminus of FGFBP3, and a secretory signal sequence is predicted with a cleavage site between position 26 (A) and 27 (R) using the SignalP 3.0 Server. An N-terminal 158-amino acid fragment of secreted human FGFBP3 (NBP-158) overlaps with the heparin binding domain but not the FGF binding domain. The amino acid sequence of NBP158 is from 27 to 184 of SEQ ID NO: 1 (FIG. 1).

Example 2: Human FGFBP3 Protein (Untagged) Expression in CHO Cells

Only secreted human FGFBP3 is found in the supernatants of CHO cells transfected with an expression vector that contains the native FGFBP3 protein without a tag (FIG. 2, A, B). Both precursors and secreted peptide of human FGFBP3 are found to migrate at an apparent molecular masse of 33 kDa and 27 kDa, respectively, in the lysates of transfected CHO cells (FIG. 2, C). To further analyze the FGFBP3 protein, conditioned medium expressing exogenous untagged human FGFBP3 (FIG. 2A) are separated on a 4-12% NUPAGE gel and proteins stained with Coomassie Blue. The predominant protein present in this fraction migrated at the same position as immunoreactive FGFBP3 (FIG. 2B). The indicated protein sample in panel A is analyzed by mass spectrometry and 100% sequence (shown as underlined) of secreted human FGFBP3 peptides are identified by LC/MS (as indicated by SEQ ID NO: 2, or FIG. 2D).

Example 3: Therapeutic Effects of FGFBP3 Treatment on Glucose Metabolism is Independent of FGF Signaling 8 week-old male ob/ob mice were purchased from Nanjing Biomedical Research Institute of Nanjing University (Nanjing, China). Animals were maintained in GLP animal facility at Laboratory Animal Center of Sun Yat-Sen University and were provided with regular rodent chow and water ad libitum. Animal experiments were reviewed and approved by the Institutional Animal Care and Use Committee (IACUC) of Sun Yat-Sen University. To confirm the activity of FGFBP3, we inject ob/ob mice with a single dose of FGFBPs and perform intraperitoneal glucose tolerance test (IPGTT). Mice were fasted overnight (16 h). Before starting the experiments, animals were weighed to determine the amount of glucose to inject. IPGTT was performed in a quiet room and handling was kept down to a minimum to reduce stress during the procedure. A bolus of glucose (1 g $kg^{-1}$) was injected into the intraperitoneal cavity (30% D-glucose:$H_2O$ solution) and blood was sampled from the tail tip at 0, 15, 30, 60, 120 and 180 min, and blood glucose levels were determined with a portable glucose meter (S60, Yuwell). The baseline of IPGTT was measured without any treatment, and the plasma glucose level is compared to the normal range (fasting plasma glucose<6.1 mmol/L, 2 hr ipGTT plasma glucose<7.8 mmol/L). FGFBP3 was administered in the morning (9:00 am) by single intraperitoneal (i.p.) injection. Glucose tolerance tests were performed and changes in body weights were measured for 3-6 weeks after the test.

Figure 4:
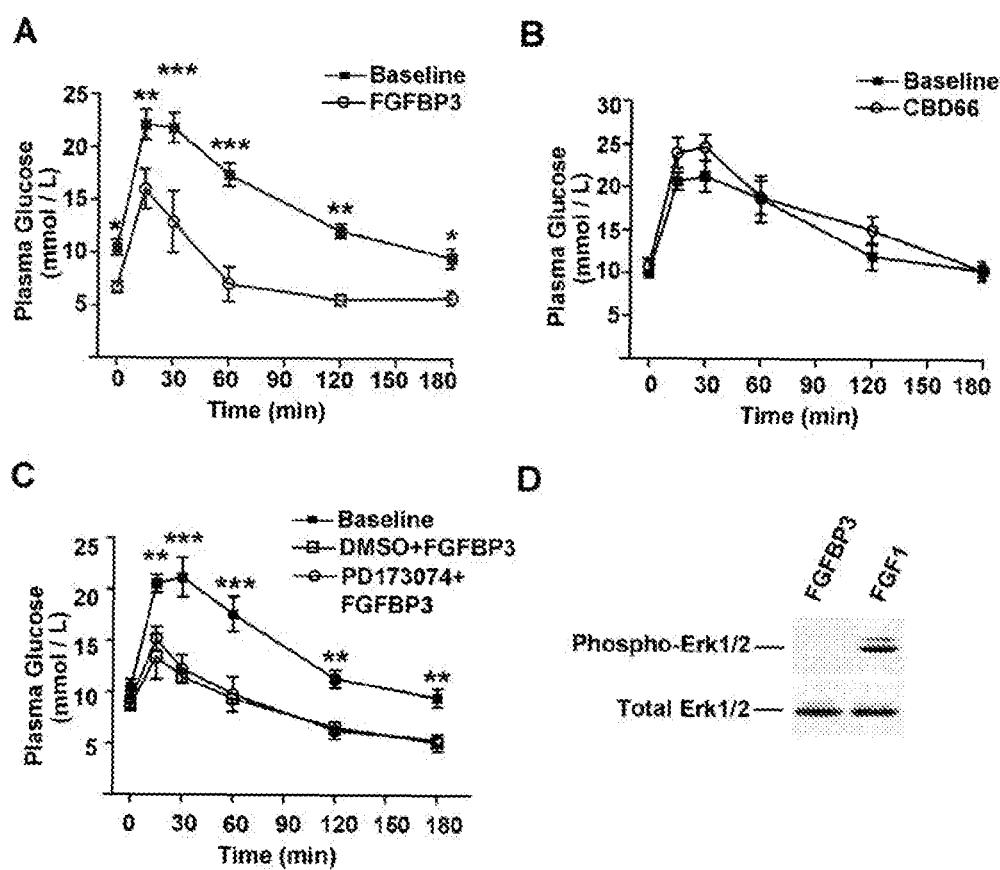
FIG. 4, Therapeutic effects of FGFBP3 treatment on glucose metabolism is independent of FGF signaling. A, 2 hrs after a single FGFBP3 treatment, the fasting glucose level is decreased and significant improvement in glucose tolerance is shown at 15, 30, 60 and 120 min (n=5). B, 2 hrs after a single treatment with CBD66, glucose metabolism is not improved in ob/ob mice (n=5). C, PD173074, a selective FGFR inhibitor, fails to block the therapeutic effects of FGFBP3 (n=5, p<0.001). (, p<0.01; *, p<0.001). D, FGFBP3 does not activate Erk1/2 signaling in HepG2 cells. Symbols ( and *) indicate significant differences in plasma glucose level before (baseline) and after FGFBP3 treatment.

2 hrs after a single FGFBP3 injection (0.5 mg/kg), the glucose tolerance is significantly improved at 60 and 90 min before and after treatment (n=5) (FIG. 4A). To evaluate the role of endogenous FGFs in FGFBP3 treatment, we systemically delivered CBD66, the FGF binding domain of FGFBP3, into ob/ob mice, and then ipGTT was performed 2 hrs after CBD66 treatment. The fasting glucose was not decreased and the glucose tolerance was not improved (FIG. 4B, n=5). Furthermore, ob/ob mice are given 5 mg/kg PD173074 (p.o.) or 20% DMSO as control. And PD173074 fails to block the glucose-lowering effect of 0.5 mg/kg FGFBP3 (FIG. 4C, n=5, p<0.001), although it prevents the increase in cerebral vascular permeability by over-expression of FGFBP3 in vivo. Furthermore, FGFBP3 treatment without exogenous FGF fails to activate Erk1/2 signaling in HepG2 cells (FIG. 4D). Since the phosphorylation of Erk1/2 is essential for all FGF signaling pathways, these results suggest that FGFBP3 treatment improves the glucose homeostasis not through FGFR activation or endogenous FGF signaling.

Example 4: Conformational Analysis of Secreted Human FGFBP3 by Hydrogen/Deuterium Exchange A member of endocrine FGFs, FGF21, has therapeutic potentials for metabolic diseases[3-7]. The clinical trial for an FGF21 mimetic shows great lipid-lowering effects but surprisingly modest effects on glucose homeostasis[8]. Previous studies show that FGFBP3 associates with endogenous FGF through CBD66 and increases cerebral vascular permeability by activating FGFR in vivo[1]. To confirm the interaction of FGF21 with FGFBP3, we analyze the conformation of secreted FGFBP3 protein (−25-0, the signal peptide sequence; 1-232, the secreted FGFBP3 protein sequence) and CBD66 (167-232) by Hydrogen-deuterium exchange (H/D exchange) mass spectrometry (MS).

The deuterium labeling and mass spectrometry analysis are briefly described here. Protein stock solutions at 30 μM in 10 mM sodium phosphate, 150 mM NaCl (pH 7.4) were used for the experiment. The mixtures of proteins: FGFBP3-FGF21 and CBD66-FGF21 were prepared by 1:1 ratio and incubated at 4° C. with gentle agitation overnight. H/D exchange reactions were initiated by diluting the stock 9-fold (v/v) with $D_2O$ buffer (10 mM sodium phosphate, pD 7.0) at 25° C. For the zero time point, the samples were diluted with 10 mM sodium phosphate buffer (pH 7.0). The isotope exchange reaction was quenched after one hour by 1:1 dilution using ice-cold 100 mM sodium phosphate buffer (pH 2.3) and then injected online into a Immobilized Pepsin Cartridge (Applied Biosystem, Thermo, USA) followed by separation using a Waters nanoACQUITY system with HDX technology for ultraperformance liquid chromatograph (UPLC) (Waters Corporation, USA) and mass analysis using a Waters Synapt-G2S HDMS mass spectrometer (Waters Corporation, USA). Protein samples (70-80 pmol) were injected on to a 2.1 mmD/30 mmL stainless steel column packed with immobilized pepsin with a flow rate of 1 μl/min in 0.1% formic acid. Peptides were trapped on a VanGuard Pre-Column (2.1 mm*5 mm, ACQUITY UPLC BEH C18, 1.7 μm) for 3 min. The trap was then placed in line with an ACQUITY UPLC BEH C18 column (1.7 μm, 1.0 mm*100 mm; Waters Corporation), and an 20%-80% gradient of acetonitrile over 9 min at a flow rate of 37 μl/min was used to separate the peptides at 0° C. Formic acid (0.1%) was added to both mobile phases to maintain a pH of 2.5. Mass spectra of peptides were acquired in positive-sensitivity ion mode using electrospray ionization on Waters Q-ToF mass spectrometer equipped with ion mobility separation under optimized conditions. Spectra were acquired over a mass-to-charge ratio (m/z) range of 50-2,000 over 12 min, collision energy ramped at 21-44V. Mass accuracy was maintained through continuous lock-mass correction using Leucine Enkephalin standard (Waters Corporation, USA). Peptic peptides of duplicate undeuterated control samples (triplicate samples for FGFBP3) were identified using a combination of accurate mass and collision-induced dissociation in data-independent acquisition mode ($MS^E$) coupled with ion mobility separation, aided by Waters MassLynx 4.1 software. Mass spectra of undeuterated and deuterated peptides at zero and one hour were extracted and analyzed in Waters DynamX v2.0.

Figure 5:
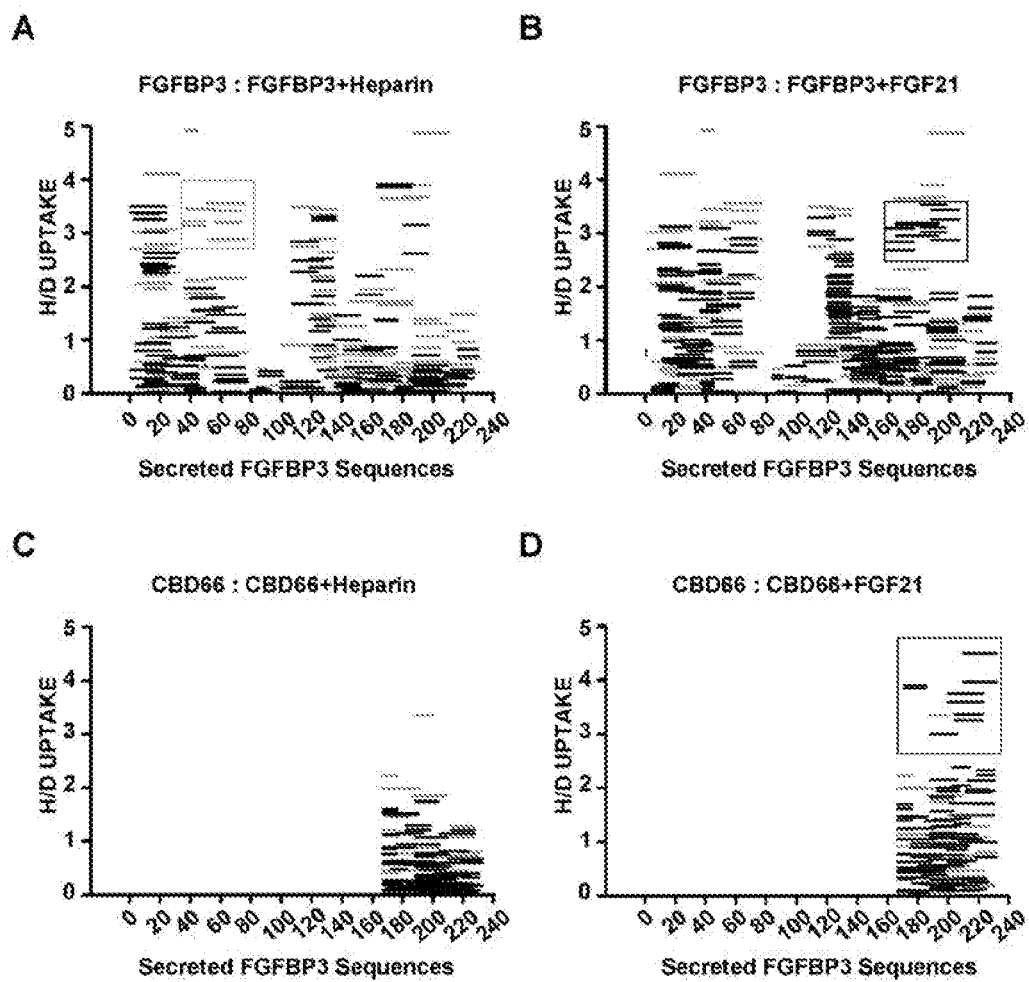
FIG. 5, Conformational analysis of secreted human FGFBP3 by Hydrogen/Deuterium exchange. FGFBP3 improves glucose tolerance independent of FGF21 signaling. (A,B) Deuterium uptake by secreted FGFBP3 and CBD66. The y-axis corresponds to the actual amount of deuterium that is incorporated into the peptides; and the x-axis represents amino acid sequences of FGFBP3 peptide fragments (−25-0, the signal peptide sequence; 1-232, the secreted FGFBP3 protein sequence; 167-232, the C-terminal 66 amino acid, CBD66). Deuterium uptake by FGFBP3 (A) or CBD66 (B) without FGF21 (----) is compared to that with FGF21 (----). The most significant difference is enclosed by the black box (□). (C,D) Deuterium uptake by FGFBP3 (C) or CBD66 (D) in the absence of heparin (----) is compared to that in the presence of heparin (----). The most significant difference is shown (□).

The deuterium uptake at 60 min by all the FGFBP3 peptide fragments is increased, which exhibits a more relaxed conformation of 1-77, 107-139 and 165-197 amino acid residues. A tight conformation is shown at 78-106 and 198-232 amino acid sequences with less deuterium uptake (FIG. 5A, ----). After incubation with FGF21, deuterium uptake of FGFBP3 fragment (158-205) (FIG. 5A, ▫) and CBD66 (167-232) (FIG. 5B, □) are both increased, indicating unfolding of this FGF21-binding domain. The conformation of FGFBP3 also changes after incubation with heparin at 4° C. overnight. Deuterium uptake of amino acids 37-77 is decreased in the presence of heparin (FIG. 5C, ----), but not changed for the predicted heparin binding domain (amino acids 82-114) by the sequence alignment of FGFBP3 and FGFBP1. The conformation of CBD66 does not change in the presence of heparin (FIG. 5C,D---- and ----), which is consistent with previous findings.

Example 5: Human FGFBP3 Mutant Protein, NBP158, Expression in CHO Cells

Figure 6:
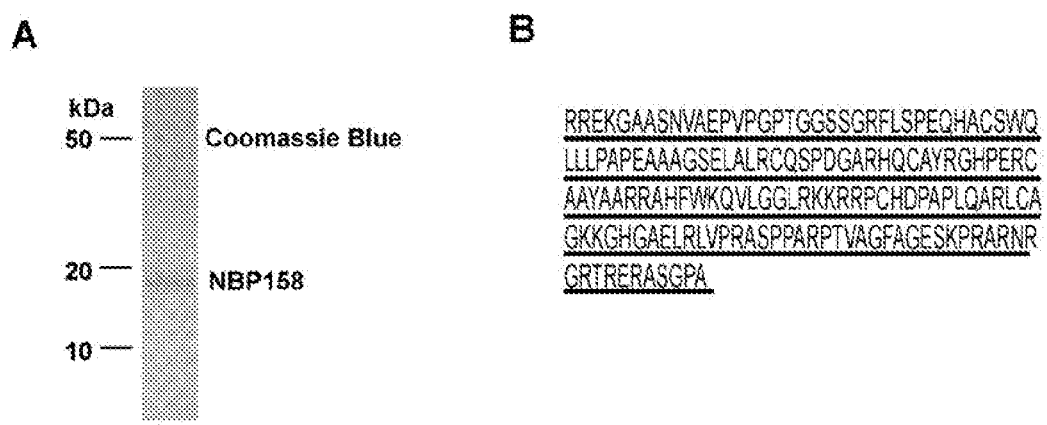
FIG. 6, Human FGFBP3 mutant protein (NBP158) expression in CHO cells. A, The N-terminal 158 amino acids of secreted human FGFBP3 (NBP158, amino acid 27-184 of SEQ ID NO:1, i.e., SEQ ID NO: 4) in conditioned culture medium of CHO cells transfected with a mutant FGFBP3 expression vector is shown by Coomassie blue staining (A). B, The indicated protein fraction in panel A is analyzed by mass spectrometry analysis and 100% sequence (shown as underlined) of NBP158 are identified by LC/MS (shown as underlined sequences).

The N-terminal 158 amino acids of secreted human FGFBP3 (NBP158, amino acid 27-184 of SEQ ID NO:1, i.e., SEQ ID NO: 4) is found in the supernatants of CHO cells transfected with an expression vector that contains the full-length NBP158 sequence (amino acid 1-184 of SEQ ID NO: 1, i.e., SEQ ID NO:5). Secreted NBP is found to migrate at an apparent molecular masse of 18 kDa (FIG. 6, A). The indicated protein sample is analyzed by mass spectrometry and 100% sequence (shown as underlined) of NBP158 is identified by LC/MS (FIG. 6B).

Example 6: Time Course of Single NBP158 Treatment on Glucose Metabolism in Ob/Ob Mice To confirm the activity of NBP158, we inject ob/ob mice with a single dose of NBP158 and perform IPGTT as described above. 2 hrs after a single NBP158 injection (0.5 mg/kg), the fasting glucose the glucose tolerance is significantly improved at 60 and 90 min before and after treatment (n=6) (FIG. 7A). To determine the time course of a single NBP158 treatment, GTT is performed at 24 hrs after a single NBP158 injection, and the fasting glucose level is not reduced, but a significant difference in glucose tolerance is found at 30 and 60 min (n=6) (FIG. 7B). 48 hrs after a single NBP158 treatment, no significant difference is shown (n=6) (FIG. 7C,D).

Figure 8:
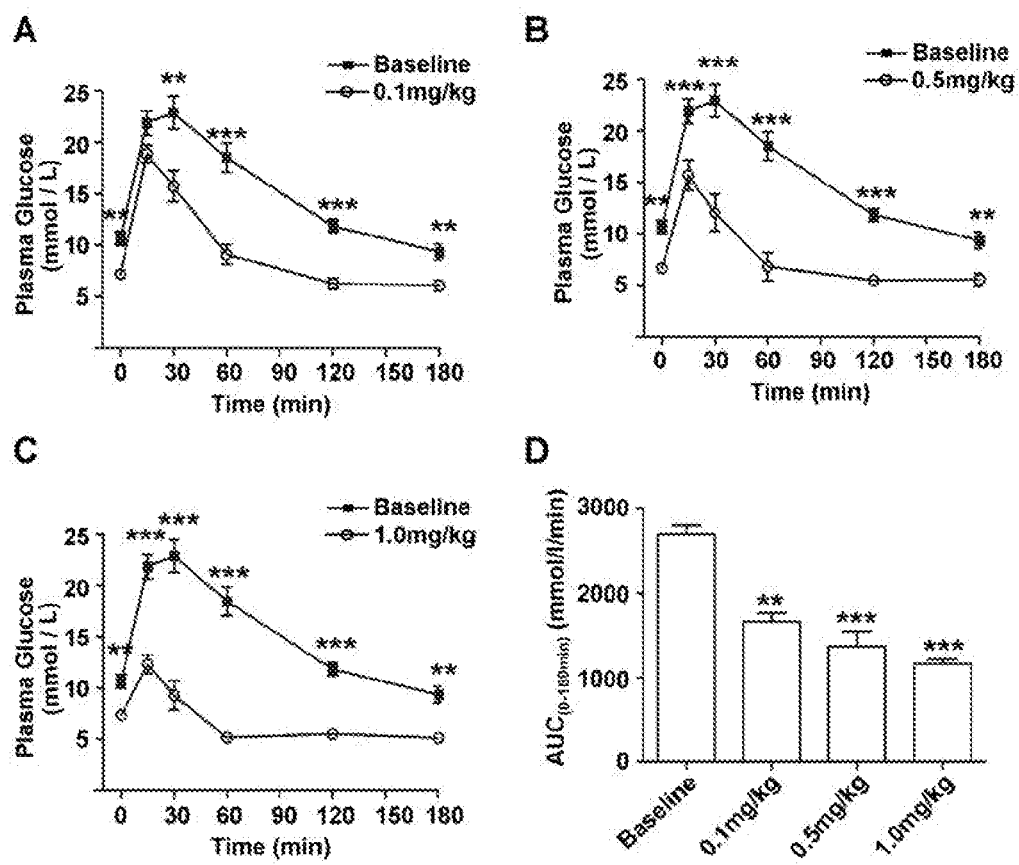
FIG. 8, Dose response of single NBP158 treatment on glucose metabolism in ob/ob mice. A-C, The fasting glucose level is decreased and significant improvement in glucose tolerance is shown at 15, 30, 60 and 120 min at 0.1 mg/kg (n=6) (A), and greater effects are found at 0.5 mg/kg (n=6) (B) and 1 mg/kg (n=6) (C). D, Decrease in fasting glucose level and improvement of glucose tolerance in DIO mice after an intraperitoneal injection of NBP158 at 0.1 mg/kg (n=6), 0.5 mg/kg (n=6) or 1.0 mg/kg (n=6). (*, p<0.05; , p<0.01; *, p<0.001).

Example 7: Dose Response of NBP158 Treatment on Glucose Metabolism in Ob/Ob Mice To evaluate the systemic effects of purified NBP158 protein, we treated ob/ob mice with increasing doses of NBP158 (0.1, 0.5, 1 mg/kg). 2 hrs after a single treatment of NBP158 (0.1 mg/kg), the fasting glucose is reduced to $7.06\pm0.15$ (mmol/L) from the baseline $10.6\pm0.7$ (mmol/L) ($p<0.01$), and the glucose tolerance is improved at 30, 60, 120 and 180 min in the glucose tolerance test (FIG. 8A, 0.1 mg/kg, $p<0.001$) (n=6). The area under the curve (AUC) is decreased by 38.4%, from $2694.54\pm125.46$ to $1659.17\pm95.83$ (mmol/l/min) (FIG. 8D, 0.1 mg/kg, $p<0.01$). Following treatment with 0.5 mg/kg NBP158, the fasting glucose was reduced to $6.65\pm0.38$ (mmol/L) ($p<0.01$), and a significantly lower plasma glucose level was also found at 15, 30, 60, 120 and 180 min (FIG. 8B, 0.5 mg/kg, $p<0.001$) (n=6). AUC is decreased by 49.2%, to $1369\pm161$ (mmol/l/min) (FIG. 8D, 0.5 mg/kg, $p<0.01$). At higher doses, NBP158 treatment reduces the fasting glucose level to $7.19\pm0.15$ (mmol/L) ($p<0.01$), and a significantly lower plasma glucose level was also found at 15, 30, 60, 120 and 180 min, with a 56.8% decrease in AUC, to $1164.67\pm35.33$ (mmol/l/min) (FIG. 8C, D, 1.0 mg/kg, $p<0.001$)(n=6).

Normal movements of these animals are observed for 3 weeks after the experiment. In fed ob/ob mice, NBP158 treatment (0.5 mg/kg) does not change the random glucose level from 15 min to 24 hours after the injection, which suggests the plasma glucose level can be maintained by food ingestion. Therefore, we conclude that NBP158 treatment dramatically reduces the plasma glucose level in a dose-dependent manner, with a rapid onset (<2 hrs) and long duration (>24 hrs).

Figure 9:
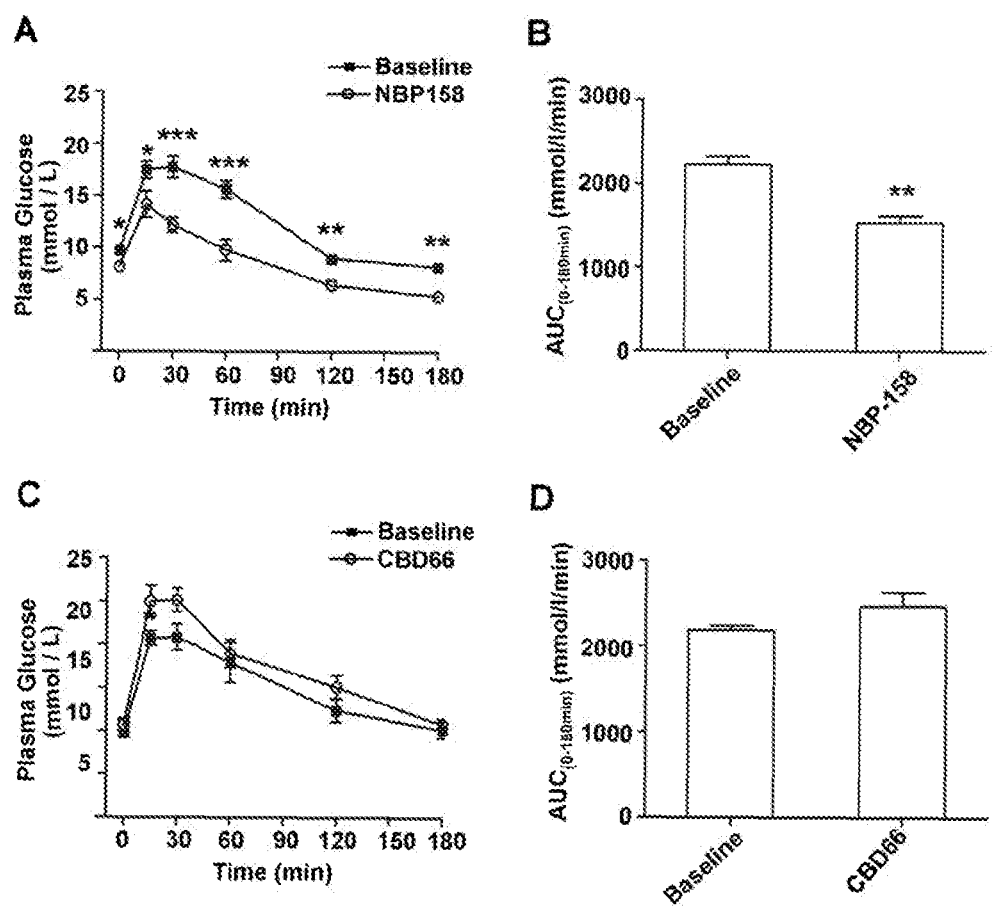
FIG. 9, Acute effects of single NBP158 treatment on glucose metabolism in diet-induced-obesity (DIO) mice. A, 2 hrs after NBP-158 single treatment, the fasting glucose level is decreased and significant improvement in glucose tolerance is shown at 15, 30, 60, 120 and 180 min (n=6). B, improvement of glucose metabolism in DIO mice after an intraperitoneal injection of NBP158 (n=6). C, 2 hrs after a single CBD66 treatment, the glucose level is not significantly different at 0, 15, 30, 60, 120 and 180 min (n=6). D, 2 hrs after a single CBD66 treatment, the glucose tolerance in DIO mice is not improved (n=6) (*, p<0.05; , p<0.01; *, p<0.001).

Example 8: Acute Effects of NBP158 Treatment on Glucose Metabolism in Diet-Induced-Obesity (DIO) Mice 3 week-old male C57BL6 mice were purchased from Sun Yat-Sen University (Guangzhou, China). Animals were fed with 60% high fat diet (Cat. No. D12492, Research Diets, Inc., NJ) and water ad libitum for 3 months before experiments. Animal experiments were reviewed and approved by the Institutional Animal Care and Use Committee (IACUC) of Sun Yat-Sen University. NBP158 polypeptide or CBD66 polypeptide are administered as described above. 2 hrs after NBP158 single treatment (0.5 mg/kg), the fasting glucose level is decreased and significant improvement in glucose tolerance is shown at 15, 30, 60, 120 and 180 min (n=6). (FIG. 9A,B). 2 hrs after a single CBD66 treatment, no significant difference is found before and after treatment (n=6) (FIG. 9C, D). Therefore, treatment with NBP158, not CBD66, reduces the fasting glucose and improves the glucose tolerance in DIO mice.

Example 9: Body Weight Changes in DIO Mice Following Single Treatment with NBP158 or CBD66

Figure 10:
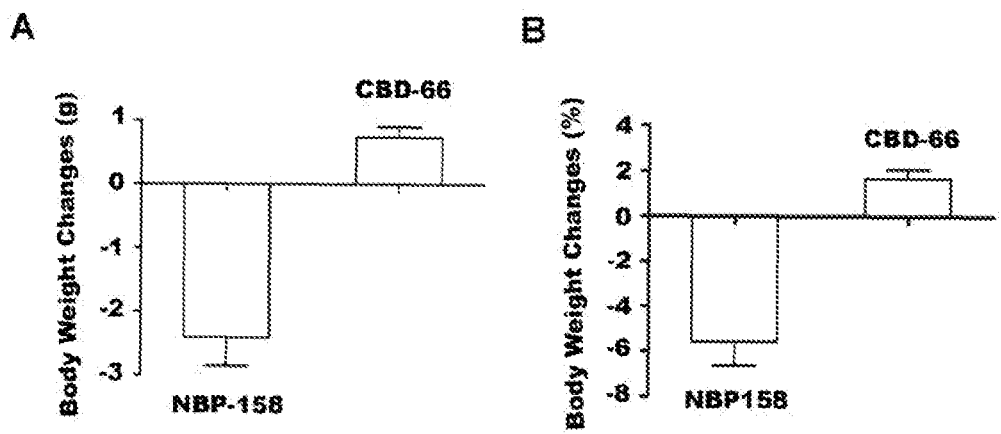
FIG. 10, Body weight changes in diet-induced-obesity (DIO) mice following single treatment with NBP-158. DIO mice (15-20 weeks old) are treated with NBP158 (n=5) or CBD66 (n=5). A week after the single treatment, mice are weighed and the changes in body weight are compared among these groups. A, In CBD66-treated group, the body weight is increased by (0.74±0.14 g/animal); in NBP158-treated group, the body weight is decreased by (2.4±0.46 g/animal). B, In CBD66-treated group, the body weight is increased by (1.66±0.42%/animal); in NBP158-treated group, the body weight is decreased by (5.545±1.08%/animal). (p<0.05)

3 weeks old male B6 mice are fed with 60% high fat diet for 12 weeks, and then randomly assigned to treatment groups with NBP158 or CBD66. DIO mice (18 weeks old) are treated with a single injection of NBP158 (n=6) or CBD66 (n=6). One week after the treatment, DIO mice were weighed and the changes in body weight were compared among these groups. In NBP158-treated group, the body weight is decreased by ($2.4\pm0.46$ g/animal) or ($5.545\pm1.08\%$/animal); and in CBD66-treated group, the body weight is increased by ($0.74\pm0.14$ g/animal) or ($1.66\pm0.42\%$/animal), which is similar to non-treated animals (FIG. 10A, B). Therefore, NBP158, not CBD66, significantly decreases the body weight, which suggests a therapeutic role in the treatment of obesity ($p<0.05$, FIG. 10).

All publications, including issued patents and published patent applications, all database entries identified by url addresses or accession numbers, and all U.S. patent applications, whether or not published, are incorporated herein by reference in their entireties.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A synthetic nucleic acid molecule consisting of (a) a DNA molecule encoding an NBP158 protein consisting of the sequence of amino acid residues from 1 to 184 or from 27 to 184 of SEQ ID NO: 1, or (b) the complement of the DNA molecule of (a).

2. The nucleic acid molecule of claim 1, wherein said nucleic acid molecule is a cDNA molecule.

3. A vector comprising the nucleic acid of claim 1.

4. The vector of claim 3 operably linked to control sequences recognized by a host cell transformed with the vector.

5. A host cell comprising the vector of claim 4.

6. The host cell of claim 5, wherein said cell is a CHO cell.

7. A process for producing an NBP158 recombinant protein comprising culturing the host cell of claim 5 or 6 under conditions suitable for expression of said NBP158 protein and recovering said NBP158 protein from the cell culture wherein the synthetic nucleic acid molecule consists of a DNA molecule encoding an NBP158 protein consisting of the sequence of amino acid residues from 1 to 184 or from 27 to 184 of SEQ ID NO: 1.

* * * * *

SEQUENCE LISTING

<160> NUMBER OF SEQ ID NOS: 5

<210> SEQ ID NO 1
<211> LENGTH: 258
<212> TYPE: PRT
<213> ORGANISM: Homo sapiens

<400> SEQUENCE: 1

Met Thr Pro Pro Lys Leu Arg Ala Ser Leu Ser Pro Ser Leu Leu Leu
1               5                   10                  15

Leu Leu Ser Gly Cys Leu Leu Ala Ala Ala Arg Arg Glu Lys Gly Ala
            20                  25                  30

Ala Ser Asn Val Ala Glu Pro Val Pro Gly Pro Thr Gly Gly Ser Ser
        35                  40                  45

Gly Arg Phe Leu Ser Pro Glu Gln His Ala Cys Ser Trp Gln Leu Leu
    50                  55                  60

Leu Pro Ala Pro Glu Ala Ala Gly Ser Glu Leu Ala Leu Arg Cys
65                  70                  75                  80

Gln Ser Pro Asp Gly Ala Arg His Gln Cys Ala Tyr Arg Gly His Pro
                85                  90                  95

Glu Arg Cys Ala Ala Tyr Ala Ala Arg Arg Ala His Phe Trp Lys Gln
            100                 105                 110

Val Leu Gly Gly Leu Arg Lys Lys Arg Arg Pro Cys His Asp Pro Ala
        115                 120                 125

Pro Leu Gln Ala Arg Leu Cys Ala Gly Lys Lys Gly His Gly Ala Glu
    130                 135                 140

Leu Arg Leu Val Pro Arg Ala Ser Pro Pro Ala Arg Pro Thr Val Ala
145                 150                 155                 160

Gly Phe Ala Gly Glu Ser Lys Pro Arg Ala Arg Asn Arg Gly Arg Thr
                165                 170                 175

Arg Glu Arg Ala Ser Gly Pro Ala Ala Gly Thr Pro Pro Gln Ser
            180                 185                 190

Ala Pro Pro Lys Glu Asn Pro Ser Glu Arg Lys Thr Asn Glu Gly Lys
        195                 200                 205

Arg Lys Ala Ala Leu Val Pro Asn Glu Glu Arg Pro Met Gly Thr Gly
    210                 215                 220

Pro Asp Pro Asp Gly Leu Asp Gly Asn Ala Glu Leu Thr Glu Thr Tyr
225                 230                 235                 240

Cys Ala Glu Lys Trp His Ser Leu Cys Asn Phe Phe Val Asn Phe Trp
                245                 250                 255

Asn Gly

<210> SEQ ID NO 2
<211> LENGTH: 232
<212> TYPE: PRT
<213> ORGANISM: Homo sapiens

<400> SEQUENCE: 2

Arg Arg Glu Lys Gly Ala Ala Ser Asn Val Ala Glu Pro Val Pro Gly
1               5                   10                  15

Pro Thr Gly Gly Ser Ser Gly Arg Phe Leu Ser Pro Glu Gln His Ala
            20                  25                  30

Cys Ser Trp Gln Leu Leu Leu Pro Ala Pro Glu Ala Ala Ala Gly Ser
        35                  40                  45

Glu Leu Ala Leu Arg Cys Gln Ser Pro Asp Gly Ala Arg His Gln Cys
    50                  55                  60

Ala Tyr Arg Gly His Pro Glu Arg Cys Ala Ala Tyr Ala Ala Arg Arg
65                  70                  75                  80

Ala His Phe Trp Lys Gln Val Leu Gly Gly Leu Arg Lys Lys Arg Arg
                85                  90                  95

Pro Cys His Asp Pro Ala Pro Leu Gln Ala Arg Leu Cys Ala Gly Lys
            100                 105                 110

Lys Gly His Gly Ala Glu Leu Arg Leu Val Pro Arg Ala Ser Pro Pro
        115                 120                 125

Ala Arg Pro Thr Val Ala Gly Phe Ala Gly Glu Ser Lys Pro Arg Ala
130                 135                 140

Arg Asn Arg Gly Arg Thr Arg Glu Arg Ala Ser Gly Pro Ala Ala Gly
145                 150                 155                 160

Thr Pro Pro Pro Gln Ser Ala Pro Pro Lys Glu Asn Pro Ser Glu Arg
                165                 170                 175

Lys Thr Asn Glu Gly Lys Arg Lys Ala Ala Leu Val Pro Asn Glu Glu
            180                 185                 190

Arg Pro Met Gly Thr Gly Pro Asp Pro Asp Gly Leu Asp Gly Asn Ala
        195                 200                 205

Glu Leu Thr Glu Thr Tyr Cys Ala Glu Lys Trp His Ser Leu Cys Asn
    210                 215                 220

Phe Phe Val Asn Phe Trp Asn Gly
225                 230

<210> SEQ ID NO 3
<211> LENGTH: 66
<212> TYPE: PRT
<213> ORGANISM: Homo sapiens
<220> FEATURE:
<221> NAME/KEY: DISULFID
<222> LOCATION: (49)..(57)

<400> SEQUENCE: 3

Ala Pro Pro Lys Glu Asn Pro Ser Glu Arg Lys Thr Asn Glu Gly Lys
1               5                   10                  15

Arg Lys Ala Ala Leu Val Pro Asn Glu Glu Arg Pro Met Gly Thr Gly
            20                  25                  30

Pro Asp Pro Asp Gly Leu Asp Gly Asn Ala Glu Leu Thr Glu Thr Tyr
        35                  40                  45

Cys Ala Glu Lys Trp His Ser Leu Cys Asn Phe Phe Val Asn Phe Trp
    50                  55                  60

Asn Gly
65

<210> SEQ ID NO 4
<211> LENGTH: 158
<212> TYPE: PRT
<213> ORGANISM: Homo sapiens

<400> SEQUENCE: 4

Arg Arg Glu Lys Gly Ala Ala Ser Asn Val Ala Glu Pro Val Pro Gly
1               5                   10                  15

Pro Thr Gly Gly Ser Ser Gly Arg Phe Leu Ser Pro Glu Gln His Ala
            20                  25                  30

Cys Ser Trp Gln Leu Leu Pro Ala Pro Glu Ala Ala Gly Ser
        35                  40                  45

Glu Leu Ala Leu Arg Cys Gln Ser Pro Asp Gly Ala Arg His Gln Cys
    50                  55                  60

```
Ala Tyr Arg Gly His Pro Glu Arg Cys Ala Ala Tyr Ala Ala Arg Arg
 65                  70                  75                  80

Ala His Phe Trp Lys Gln Val Leu Gly Gly Leu Arg Lys Lys Arg Arg
                 85                  90                  95

Pro Cys His Asp Pro Ala Pro Leu Gln Ala Arg Leu Cys Ala Gly Lys
            100                 105                 110

Lys Gly His Gly Ala Glu Leu Arg Leu Val Pro Arg Ala Ser Pro Pro
        115                 120                 125

Ala Arg Pro Thr Val Ala Gly Phe Ala Gly Glu Ser Lys Pro Arg Ala
        130                 135                 140

Arg Asn Arg Gly Arg Thr Arg Glu Arg Ala Ser Gly Pro Ala
145                 150                 155

<210> SEQ ID NO 5
<211> LENGTH: 184
<212> TYPE: PRT
<213> ORGANISM: Homo sapiens

<400> SEQUENCE: 5

Met Thr Pro Pro Lys Leu Arg Ala Ser Leu Ser Pro Ser Leu Leu Leu
  1               5                  10                  15

Leu Leu Ser Gly Cys Leu Leu Ala Ala Ala Arg Arg Glu Lys Gly Ala
                 20                  25                  30

Ala Ser Asn Val Ala Glu Pro Val Pro Gly Pro Thr Gly Gly Ser Ser
             35                  40                  45

Gly Arg Phe Leu Ser Pro Glu Gln His Ala Cys Ser Trp Gln Leu Leu
 50                  55                  60

Leu Pro Ala Pro Glu Ala Ala Gly Ser Glu Leu Ala Leu Arg Cys
 65                  70                  75                  80

Gln Ser Pro Asp Gly Ala Arg His Gln Cys Ala Tyr Arg Gly His Pro
                 85                  90                  95

Glu Arg Cys Ala Ala Tyr Ala Ala Arg Arg Ala His Phe Trp Lys Gln
            100                 105                 110

Val Leu Gly Gly Leu Arg Lys Lys Arg Arg Pro Cys His Asp Pro Ala
        115                 120                 125

Pro Leu Gln Ala Arg Leu Cys Ala Gly Lys Lys Gly His Gly Ala Glu
130                 135                 140

Leu Arg Leu Val Pro Arg Ala Ser Pro Pro Ala Arg Pro Thr Val Ala
145                 150                 155                 160

Gly Phe Ala Gly Glu Ser Lys Pro Arg Ala Arg Asn Arg Gly Arg Thr
                165                 170                 175

Arg Glu Arg Ala Ser Gly Pro Ala
            180
```